United States Patent
Fang et al.

(10) Patent No.: US 9,804,185 B2
(45) Date of Patent: Oct. 31, 2017

(54) APPLICATION METHOD FOR AUTOMATIC MICRO DROPLET ARRAY SCREENING SYSTEM WITH PICOLITER SCALE PRECISION

(71) Applicant: ZHEJIANG UNIVERSITY, Hangzhou, Zhejiang Province (CN)

(72) Inventors: Qun Fang, Hangzhou (CN); Ying Zhu, Hangzhou (CN); Yunxia Zhang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 197 days.

(21) Appl. No.: 14/758,482

(22) PCT Filed: Nov. 8, 2013

(86) PCT No.: PCT/CN2013/086729
§ 371 (c)(1),
(2) Date: Jun. 29, 2015

(87) PCT Pub. No.: WO2014/101575
PCT Pub. Date: Jul. 3, 2014

(65) Prior Publication Data
US 2016/0202281 A1    Jul. 14, 2016

(30) Foreign Application Priority Data
Dec. 31, 2012  (CN) .......................... 2012 1 0589055

(51) Int. Cl.
*G01N 35/10*     (2006.01)
*G01N 35/00*     (2006.01)
(Continued)

(52) U.S. Cl.
CPC .......... *G01N 35/1016* (2013.01); *B01L 3/021* (2013.01); *B01L 3/50273* (2013.01);
(Continued)

(58) Field of Classification Search
CPC ..... G01N 35/1016; G01N 2035/00158; G01N 2035/1039; G01N 2035/1046;
(Continued)

(56) References Cited

U.S. PATENT DOCUMENTS 6,203,759 B1 * 3/2001 Pelc ...................... B01L 3/0268
222/333
8,465,707 B2 * 6/2013 Curran ................ B01F 13/0071
422/501
(Continued)

FOREIGN PATENT DOCUMENTS

CN    1422185 A    6/2003
CN    1818662 A    8/2006
(Continued)

*Primary Examiner* — Brian R Gordon
(74) *Attorney, Agent, or Firm* — Jiwen Chen

(57) ABSTRACT

This invention is related to high-throughput screening field, in particular to an application method for automatic micro droplet array screening system of picoliter scale precision. According to this invention, the fluid driving system and the capillary are fully filled with fluid of low thermal expansion coefficient as the carrier fluid to thoroughly empty air bubbles in the capillary; after that, immersing the sampling end of capillary into the oil phase that is mutually immiscible with aqueous sample to aspirate a section of oil phase into the capillary for isolation of aqueous sample and carrier fluid; once completed, immersing the sampling end of capillary into the sample/reagent storage tube to aspirate a certain volume of aqueous sample into the capillary; finally, moving the sampling end of capillary to the oil phase above microwells on microwell array chip, and pushing the sample solution in the capillary into microwells to form sample droplet. Quantitative metering of fluid and droplet generation according to this invention are provided with volume precision in picoliter, which can effectively minimize the (Continued)

consumption of sample/reagent, and save the testing cost during high-throughput screening.

9 Claims, 3 Drawing Sheets

(51) Int. Cl.
  *B01L 3/00* (2006.01)
  *B01L 3/02* (2006.01)
(52) U.S. Cl.
  CPC .. *B01L 3/502715* (2013.01); *G01N 35/00029* (2013.01); *B01L 3/50853* (2013.01); *B01L 2200/0605* (2013.01); *B01L 2200/0642* (2013.01); *B01L 2200/0673* (2013.01); *B01L 2200/0684* (2013.01); *B01L 2200/14* (2013.01); *B01L 2200/142* (2013.01); *B01L 2300/0819* (2013.01); *B01L 2300/0896* (2013.01); *B01L 2400/0406* (2013.01); *B01L 2400/0478* (2013.01); *G01N 2035/00158* (2013.01); *G01N 2035/1034* (2013.01); *G01N 2035/1039* (2013.01)
(58) Field of Classification Search
  CPC ....... G01N 2035/1034; B01L 3/502769; B01L 2200/0605; B01L 2200/0673; B01L 3/021; B01L 3/022; B01L 3/0289
  See application file for complete search history.

(56) References Cited

U.S. PATENT DOCUMENTS

| | | | | |
|---|---|---|---|---|
| 8,809,070 B2* | 8/2014 | Saito | ................. | G01N 35/1016 422/501 |
| 2003/0213905 A1* | 11/2003 | Lennon | ................. | B01L 3/0262 250/288 |
| 2004/0050861 A1* | 3/2004 | Lisec | ................. | B01L 3/022 222/57 |
| 2009/0288710 A1* | 11/2009 | Viovy | ................. | B01L 3/0293 137/1 |
| 2012/0045765 A1* | 2/2012 | Curran | ................. | B01F 13/0071 435/6.12 |
| 2012/0328487 A1* | 12/2012 | Saito | ................. | G01N 35/1016 422/501 |
| 2014/0106467 A1* | 4/2014 | Hutter | ................. | B01L 3/021 436/180 |

FOREIGN PATENT DOCUMENTS

| | | |
|---|---|---|
| CN | 101151370 A | 3/2008 |
| CN | 101957383 A | 1/2011 |
| CN | 102553665 A | 7/2012 |
| CN | 103008037 A | 4/2013 |
| WO | WO2012/100205 A2 | 7/2012 |

* cited by examiner

APPLICATION METHOD FOR AUTOMATIC MICRO DROPLET ARRAY SCREENING SYSTEM WITH PICOLITER SCALE PRECISION

This is a U.S. national stage application of PCT Application No. PCT/CN2013/086729under 35 U.S.C. 371, filed Nov. 8, 2013 in Chinese, claiming the priority benefit of Chinese Application No. 201210589055.1, filed Dec. 31, 2012, which is hereby incorporated by reference.

FIELD OF THE INVENTION

The present invention is related to high-throughput screening field, in particular to an application method for automatic micro droplet array screening system with picoliter scale precision.

BACKGROUND ART

High-throughput screening system originates from pharmaceutical screening studies, which mainly use 96 or 384 well plate as the reactor array to distribute fluids, and mix sample/reagent with the help of automatic robots. It can realize a throughput of at least 10,000 assays per day through analysis and processing of test results with testing devices and data processing software with high sensitivity and high speed. Due to its powerful screening and analyzing capability, high-throughput screening technique has been further applied to numerous scientific areas, such as biology, medical science and chemistry. However, multiple-well plate based commercial high-throughput fluid processing and screening system is increasingly confronted with an enormous challenge accompanied by rapid increase in new targets and samples. Chemical compounds used for screening are mainly obtained from artificial synthesis or separation and purification of natural products, which may result in high cost. Currently, consumption volume of samples for multiple-well plate based high-throughput screening system is between 1 and 100 microliters. It will be possible to reduce the cost by 1,000-100,000 times if it is able to screen samples through manipulating fluids on the picoliter or nanoliter scale. Therefore, most of the studies in both industrial and academic fields focus on miniaturization of high-throughput screening systems. For instance, the minimum fluid processing volume of OryxNano series fluid processing device as developed by British Douglas company is 100 nanoliters (http://www.douglas.co.uk/oryxnano.htm); whereas that of Mosquito series fluid processing device as developed by British TTPLabTech company is down to 25 nanoliters (www.ttplabtech.com/products/mosquito/). Application of such instruments has significantly reduced the screening and R&D cost. Nevertheless, presently there still a lack of techniques and devices for manipulation and high-throughput screening of fluids at several nanoliters or picoliters scales.

Difficulties in performing high-throughput screening at picoliter scale are mainly reflected on the following aspects: 1) existing instruments are unlikely to realize reliable manipulations of fluids at picoliter scale, such as accurate metering and handling of fluids and mixing of sample/reagent; 2) evaporation effect is to be significantly with the reduction of fluid volume; for instance, aqueous phase droplet of one picoliter is to be thoroughly evaporated within 1 second under the typical laboratory conditions; 3) since the fluid in the micro system has an extremely large specific surface area, molecular self-assembly or nonspecific interactions at water/air interface and water/solid interface may result in inactivation, loss, and cross contamination to bioactive molecules, leading to false positive or negative of screening results.

The droplet based microfluidic technique serves as one of active areas for high-throughput screening miniaturization studies. It aims to realize massive generation of droplet micro-reactor of water-in-oil or oil-in-water types, mixing and reaction of samples as well as analysis and verification through control of multi-phase fluids microchannel at micron scale. The volumes of droplet rectors can be flexibly adjusted at picoliter and nanoliter scale, which makes it possible to realize high-throughput screening with extremely low consumption. Evaporation and dilution of solvents inside the droplet reactor as well as the cross contamination among samples can be effectively minimized due to the protection of the oil phase. Self-assembly effect of biologically compatible surfactant on the droplet-oil surface can provide a mild and uniform microenvironment for biochemical screening and reaction, which is favorable for improving the accuracy of analysis and screening. Meanwhile, limited volume of a droplet reactor can also accelerate the mass transfer, and improve reaction efficiency. Therefore, it is possible that the droplet-based microfluidic technique may become a new generation of high-throughput screening technique due to its excellent properties.

Presently, there are three droplet based microfluidic screening methods, namely droplet cartridge method, slipchip method and droplet assembling method. In droplet cartridge method, first, droplet capillary loads samples to be screened to the capillary to form droplet through sequential aspiration. Second, the capillary is connected to the channel of a microfluidic chip to inject target solution into the droplet for reaction via a T-shape interface on the chip. Finally, the droplet reactor formed is collected into another capillary for incubation reaction and testing (Zheng B., Ismagilov R. F. Angew. Chem., Int. Ed., 2005, 44, 2520). According to the Slipchip method, samples to be screened are loaded into the groove array on the lower chip to form droplet. After that, the upper chip is slid to mix the target reagent solution inside the channel on the upper chip with droplet on the lower chip for triggering reaction and screening (Du W. B., Li L., Nichols K. P., Ismagilov R. F. LabChip, 2009, 9, 2286). However, aforesaid two methods require manual loading of droplets, connection of capillary and channel on the chip and precise chip sliding, which are unlikely to be applied to screening of samples on a large scale. Droplet assembling method is capable of achieving the mixing of samples to be screened and reagent during the formation of droplets through quick automatic switching between the sample and reagent tube. After that, the droplets are to be stored to the capillaries and chips for reaction and test (Du W. B., Sun M., Gu S. Q., Zhu Y., Fang Q. Anal. Chem., 2010, 82, 9941, Fang Qun, Du Wenbin and Sun Meng, Sequential Droplet Technique Based Microfluidic Droplet Generation System and Its Application Methods, Chinese Invention Patent, Application No.: 201010250945.). Despite of the fact that sequential droplet assembling technique has solved the problem of automatic screening of samples on a large scale, it is difficult to accelerate the screening process due to the sequential assembling method for generation of droplets containing samples and reagent. Furthermore, due to scale effect as brought forth by miniaturization, aforesaid several droplet screening methods are unlikely to realize biological screening and test in picoliter scale.

There are mainly two methods for parallel addition of reagents into the microfluidic droplet system. The first method uses one T-shape branch channel to inject the same reagent into different droplets in the main channel (Zheng B. Ismagilov R. F. Angew. Chem., Int. Ed., 2005, 44, 2520). Normally, such method is used in combination with aforesaid droplet cartridge method for droplet based micro screening. However, the major problem with this method lies in excessive accumulation of residual droplet samples at the intersection of the T-shape channel, which may result in cross contamination to droplet. Another method makes use of droplet mixing technique for parallel injection of reagents. First, mutually paired sample and reagent droplets are produced in the microchannel; Second, hydrodynamic or dielectric approaches are used to make each paired droplets fused into a single micro reactor (the S Y, Lin R. Hung L. H., Lee A. P., Lab Chip, 2008, 8:198). However, such method is complicated in channel structure and difficult in processing, which is unlikely to be used to the screening system containing a large quantity of different samples. Moreover, aforesaid two methods are unlikely to be realized without many manual adjustments such as complicated flow rate regulation, control of droplet frequency and size, as well as feedback recording of droplet compositions. Therefore, it is unavailable for reliable automation, and thus is difficult for instrument industrialization.

DISCLOSURE OF THE INVENTION

Technical Issues

The object of the present invention is to provide an application method for automatic micro droplet array screening system with picoliter resolution. Such system is available for fully automatic metering of fluids in picoliter, formation of array of different sample droplets, parallel quantitative addition of target reagents and reaction tests in minimum volume. It is applicable to high-throughput screening of drug, screening of catalysts, study of enzyme kinetics, disease diagnosis and analysis of single cells and molecules.

Solutions

Technical solutions of the present invention are stated as follows:

An application method for automatic micro droplet array screening system with picoliter scale precision, comprising a capillary, a fluid driving system, a microwell array chip, a sample/reagent storage tube and an automated translation stage, of which specific procedures are stated as follows:

1) Fully filling the fluid driving system and capillary with a fluid of low expansion coefficient as the carrier fluid, and thoroughly removing air bubbles inside the capillary;

2) Immersing the sampling end of the capillary into the oil phase that is not soluble in the aqueous samples to aspirate a plug of the oil phase into the capillary for isolation of aqueous samples and carrier fluids;

3) Immersing the sampling end of the capillary into the sample/reagent storage tube to aspirate a certain volume of aqueous samples into the capillary;

4) Moving the sampling end of the capillary into the oil phase above microwells on the microwell array chip, and pushing the sample inside the capillary into the microwells to form sample droplets.

The Step 4) of the present invention further comprises the following specific steps:

a) Generating droplets of multiple samples to be screened with different chemical compositions or concentrations on the microwell array chip;

b) Aspirating a large volume of reagents at one time into the capillary, and respectively inserting the sampling end of the capillary into each sample droplet; respectively injecting a certain volume of reagent to form a droplet reactor, and complete mixing of sample and reagent, reaction, testing and screening.

Step 4) of the invention also comprises the following steps:

m) Producing a large number of reagent droplets on the microwell array chip;

n) Respectively injecting sample solution to be screened into each reagent droplet to form droplet reactor, and complete mixing of reagent and sample, reaction, testing and screening.

The fluid driving system in the present invention is provided with fluid driving precision of several nanoliters/minute, in which flow rate of driven fluid ranges from 1 nanoliters/minute to 500 nanoliters/minute.

According to the present invention, to eliminate mechanical backlash during switchover from aspiration to push-out or from push-out to aspiration when changing fluid driving orientation of the fluid driving system, and ensure fluid metering precision in picoliter scale, an additional volume of oil phase is to be aspirated into the capillary in advance before aspiration of aqueous sample or reagent solution. It is also necessary to push the additional oil phase out of the capillary when pushing sample or reagent solution out of the capillary.

The fluid driving system and capillary of the present invention are fully filled with a fluid of low thermal expansion coefficient as the carrier fluid to prevent the impact of temperature fluctuation during test on fluid driving precision. The thermal expansion coefficient of the carrier fluid ranges from 0.00001/° C. to 0.0005/° C.

The capillary of the present invention has a thinner wall that is favorable for fluid metering in picoliter scale and reduction in residual fluid on the capillary end. The wall thickness of the capillary ranges from 1 micron to 100 microns.

According to the application method for the automatic micro droplet array screening system with picoliter scale precision of the present invention, it is essential to degas the carrier fluid and oil phase before application to prevent generation of air bubbles during fluid driving.

During the application of the present invention, a layer of oil phase immiscible with aqueous phase is covered on the microwells of microwell array chip and sample/reagent storage tubes to prevent evaporation or contamination of micro droplet, sample and reagent as exposed to the air. The thickness of oil phase ranges from 0.1 mm to 10 mm.

During the application of the present invention, a biologically compatible surfactant is added into the oil phase to eliminate interference of oil phase on micro biochemical reaction. This is to make use of self-assembling effect of surfactant molecules at oil/water interface to minimize absorption and deactivation of biological molecules at the interface. The concentration of surfactant ranges from 0.01% to 10%.

Beneficial Effects of the Present Invention

The present invention has the following advantages: (1) it ensures volume precision in picoliter scale for quantitative metering of fluid and generation of droplets, effectively reduces consumption of samples/reagents during high-throughput screening, and saves test cost; (2) by inserting the capillary into the droplet of sample to be screened, and continuously injecting reagents to complete mixing of sample and reagent, reaction, test and screening, the present invention effectively improves screening throughput, and minimizes risks of cross contamination; (3) the present invention realizes full automation fluid metering, push-out, droplet generation and reagent injection, and effectively minimizes artificial mistakes and errors to facilitate industrialization and extensive popularization of the system.

Figure 1:
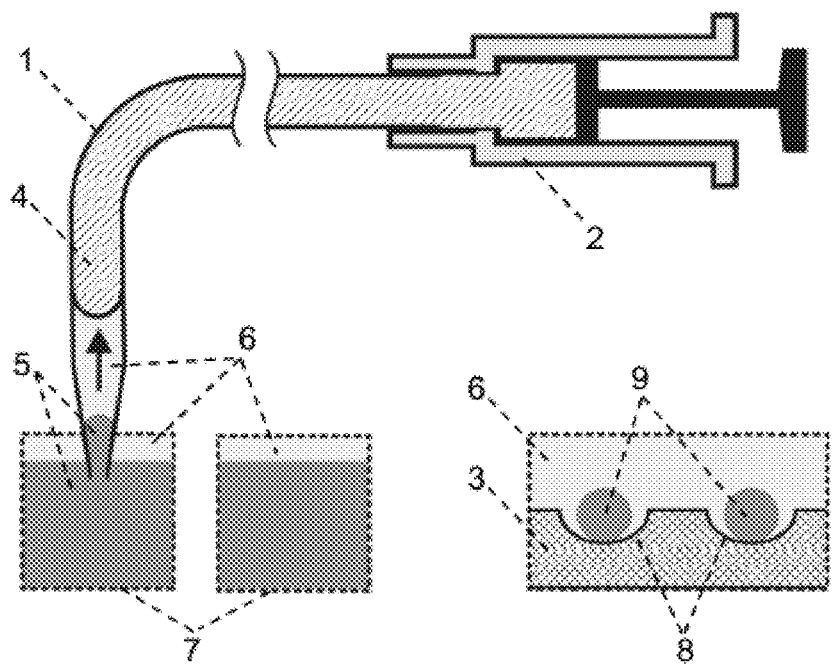
FIG. 1 is the diagram for the droplet array screening system with picoliter scale precision and its application methods.

1-Capillary, 2-Fluid driving system, 3-Microwell array chip, 4-Carrier Fluid, 5-Aqueous sample, 6-Oil phase, 7-Sample/reagent storage tube, 8-Microwell, 9-Sample droplet, 10-Reagent, 11-Droplet reactor.

Preferred Embodiments Of The Present Invention:

Detailed description of technical solutions to the present invention is stated as follows:

The present invention is related to a micro droplet array screening system with picoliter scale resolution, comprising a capillary, a fluid driving system, a microwell array chip, a fluid driving system, a sample/reagent storage tube, and an automated translation stage. The fluid driving system is connected with the capillary for quantitative aspiration and push-out of fluid in small volume; sample/reagent storage tube and microwell array chip are fixed to the automated translation stage that is available for three dimensional (3D) moving; the sample/reagent storage tube is used for storage of samples and reagent as required by tests; the microwell array chip is used for storage, reaction, test and screening of micro droplets.

According to the present invention, the application method of the automatic micro droplet array screening system with a picoliter scale precision is stated as follows: First, fully filling the fluid driving system and capillary with a fluid of low thermal expansion coefficient as the carrier fluid, and thoroughly removing air bubbles inside the capillary; second, immersing the sampling end of the capillary into the oil phase that is not soluble in the aqueous samples to aspirate a plug of oil phase into the capillary for isolation of aqueous samples and the carrier fluid; third, immersing the sampling end of the capillary into the sample/reagent storage tube to aspirate a certain volume of aqueous sample into the capillary;

finally, moving the sampling end of the capillary into the oil phase above microwells on the microwell array chip, and pushing the sample inside the capillary into the microwells to form sample droplets.

According to the present invention, multiple sample droplets to be screened with different chemical compositions or concentrations on the microwell array chip are produced in an attempt to improve the screening throughput; after that, a large volume of reagent are aspirated at one time into the capillary, and the sampling end of the capillary is respectively inserted into each sample droplet; a certain volume of reagent is respectively injected to form a droplet reactor, and mixing of samples and reagent, reaction, testing and screening are completed. As another solution, it is also applicable to produce a large number of reagent droplets with the same chemical composition and concentration on the microwell array chip, and respectively inject sample solutions of varied chemical compositions and concentrations into the reagent droplets for screening to form the droplet reactors, and complete mixing of reagent and samples, reaction, test and screening.

According to the present invention, the fluid driving system is available for positive push-out and reverse aspiration of the fluid at the flow rate ranging from 1 picoliter/minute to 100 microliters/minute; the volume of fluid as metered ranges from 1 picoliter to 100 microliters. In a preferred embodiment, to accomplish metering of the fluid in picoliter scale, the fluid driving system is provided with a fluid driving precision of several nanoliters/minute with a flow rate of driven fluid ranging from 1 nanoliter/minute to 500 nanoliters/minute; the volume of the fluid as metered ranges from 1 picoliter to 1,000 microliters According to the present invention, to eliminate mechanical backlash (during switchover from aspiration to push-out or from push-out to aspiration) when changing fluid driving orientation of the fluid driving system, and ensure fluid metering precision in picoliter scale, an additional volume of oil phase is to be aspirated into the capillary in advance before aspiration of aqueous sample or reagent solutions. It is also necessary to aspirate additional oil phase into the capillary when pushing sample or reagent solutions out of the capillary.

According to the present invention, a fluid of low thermal expansion coefficient and fully filled the fluid driving system and capillary is used as the carrier fluid to prevent impact of temperature fluctuation during test on fluid driving precision. In a preferred embodiment, thermal expansion coefficient of the carrier fluid ranges from 0.00001/° C. to 0.0005/° C.

According to the present invention, to realize fluid metering in picoliter scale and reduction in residual fluid on the sampling end of the capillary, it is essential to proceed with sharpening treatment to the sampling end of the capillary in an attempt to reduce the diameter and cross section of the tip of the sampling end. In a preferred embodiment, the diameter of the sampling tip ranges from 1 micron to 100 microns. Meanwhile, hydrophobic treatment is conducted to the inner wall of the capillary and outer wall of the sampling end.

According to the present invention, the capillary of the present invention has a thinner wall that is favorable for fluid metering in picoliter scale and reduction in residual fluid inside the capillary. In a preferred embodiment, the wall thickness of the capillary ranges from 1 micron to 100 microns.

According to the present invention, degassing (vacuum or ultrasonic) is conducted to the carrier fluid and oil phase before application to prevent generation of air bubbles during fluid driving. Air bubbles may significantly reduce the fluid metering precision in picoliter.

According to the present invention, before aspiration of sample (or reagent) solutions, a plug of oil phase that is mutually immiscible with the sample (or reagent) is aspirated to isolate the sample (or reagent) and carrier fluid of low thermal expansion coefficient. In a preferred embodiment, oil phase length ranges from 50 microns to 20 millimeters.

According to the present invention, multiple microwells for containing small volumes of fluid are to be prepared on the microwell array chip. The volume of each microwell ranges from 1 picoliter to 100 microliters.

According to the present invention, a layer of oil phase is to be covered on the microwells of microwell array chip and sample/reagent storage tubes to prevent evaporation or contamination of micro droplet and sample as exposed to the air. The thickness of oil phase ranges from 0.1 mm to 10 mm. In case of application, a layer of oil phase immiscible with aqueous phase is covered on the microwells of microwell array chip and sample/reagent storage tubes to prevent evaporation or contamination of micro droplet, sample and reagent as exposed to the air. In a preferred embodiment, thickness of oil phase ranges from 0.1 mm to 10 mm.

In a preferred embodiment according to the present invention, biologically compatible surfactant is added into the oil phase to eliminate interference of oil phase on micro biochemical reaction during screening and reaction. This aims to make use of self-assembling effect of surfactant molecules at oil/water interface to minimize absorption and deactivation of biological molecules at the interface. In a preferred embodiment, concentration of surfactant ranges from 0.01% to 10%.

According to the present invention, multiple capillaries and fluid driving devices are used simultaneously for metering and push-out of large number of fluid samples/reagents as well as generation of droplets.

Further description of technical solutions of the present invention in combination with preferred embodiments is stated as follows:

Referring to drawings, detailed description of preferred embodiments according to the present invention is stated as follows:

FIG. 1 is the diagram for droplet array screening system with a picoliter scale precision and its application methods. The application method is stated as follows: capillary 1 is used as the sampling probe, and its end is connected to a fluid driving system 2. The capillary 1 and fluid driving system 2 are fully filled with the fluid of low thermal expansion coefficient as the carrier fluid 4, and a plug of oil phase 6 that is mutually immiscible with aqueous phase is introduced from the sampling end of capillary 1 to isolate aqueous sample 5 and carrier fluid 4. The capillary 1 or sample/reagent storage tube 7 is moved to immerse the sampling end of the capillary 1 into the oil phase 6 to aspirate additional volume of oil phase 6 into the sampling end of the capillary 1. The sampling end of capillary 1 is further immersed into sample 5 for quantitative aspiration of a certain volume of the sample 5. After that, the capillary 1 or microwell array chip 3 is further shifted again to place the sampling end of the capillary 1 on oil phase 6 above microwells on the chip 3. The fluid driving system 2 is started to push the fluid of sample 5 and a small volume of additionally aspirated oil phase 6 inside capillary 1 to the microwell 8 to form a small volume of the droplet 9 of the aqueous sample 5.

The sharpening treatment is conducted to the sampling end of the capillary 1 and hydrophobic surface treatment to inner and outer wall of the capillary 1 and the surface of the microwell array chip 3 before generation of the micro droplet array with this system. The vacuum degassing or ultrasonic degassing treatment is conducted to the carrier fluid 4 and oil phase 6 to prevent generation of air bubbles during fluid driving.

Figure 2:
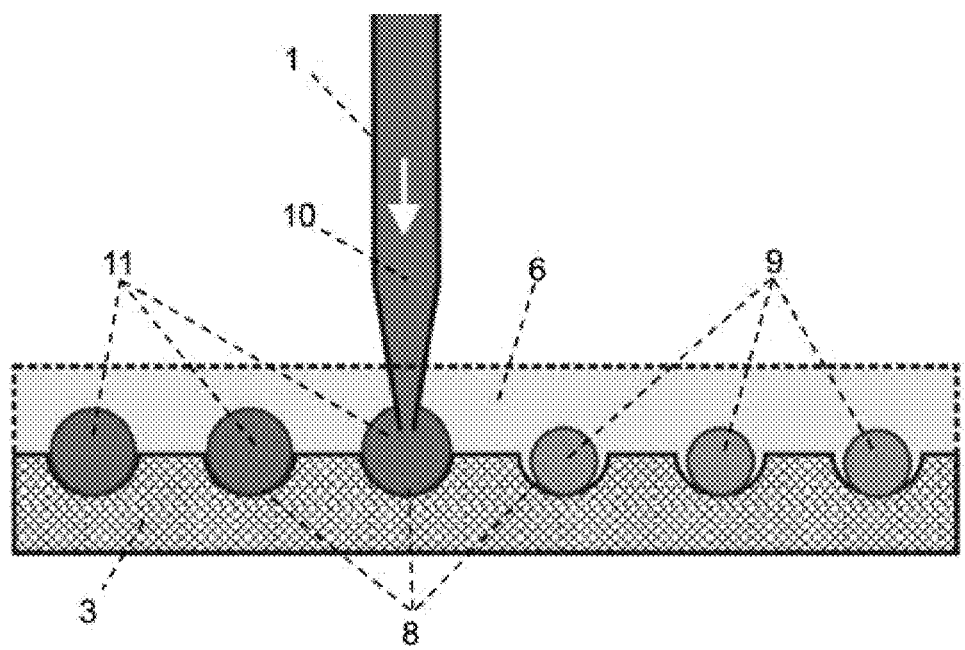
FIG. 2 is the diagram for sequential injection of reagent into the sample droplets to be screened by inserting the capillary into the droplets.

FIG. 2 is the diagram for sequential injection of reagent into the sample droplets to be screened by inserting the capillary into the droplet. According to the method as shown in FIG. 1, the array for sample droplet 9 of different chemical compositions or concentrations is to be generated on microwell array chip 3. A large volume of reagent 10 is aspirated into capillary 1, and then capillary 1 or microwell array chip 3 is moved to respectively insert the sampling end of capillary 1 into each sample droplet 9; The fluid driving system 2 is started to push a certain volume of the reagent 10 into each sample droplet 9 to complete mixing of sample/reagent and formation of the droplet reactor 11.

Embodiment 1

Figure 3:
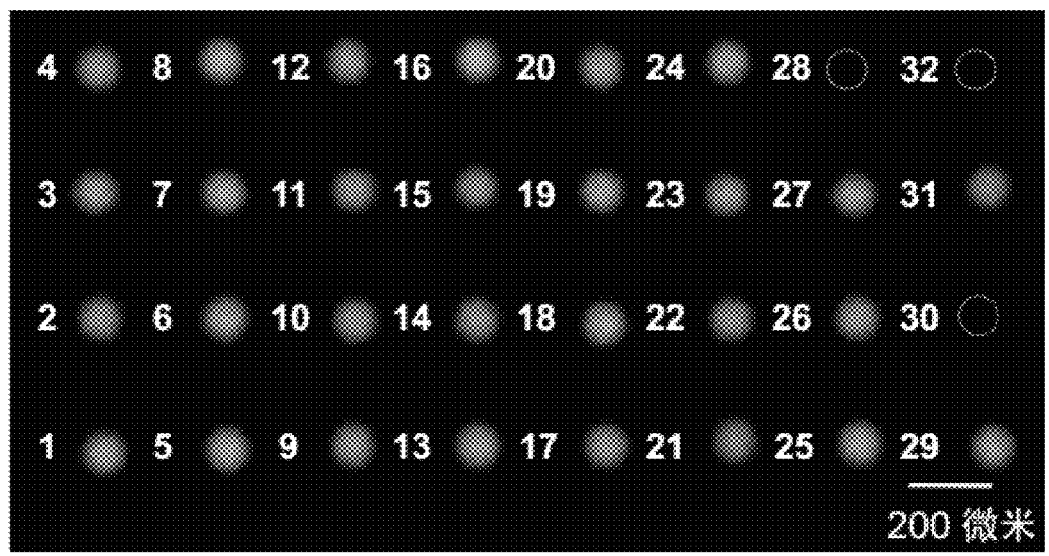
FIG. 3 is the aerial fluorescent image for screening of Caspase-1enzyme inhibitor with the droplet array screening system.

FIG. 3 is the aerial fluorescent image for screening of enzyme inhibitor according to the droplet array screening system and its application method as shown in FIGS. 1 and 2 by taking 32 small-molecule compounds as samples for screening and Caspase-1 as the screening target. Firstly, 100 µM small-molecule compounds were placed into the sample/reagent storage tubes. The droplets of 32 small-molecule compounds were generated on the microwell array chip with the droplet array generation method as shown in FIG. 1. The volume of each droplet is 180 picoliters. After that, 180 picoliters of Caspase-1 enzyme (6 mU/µL) and substrate (Z-YVAD-R110) solution (20 µM) were respectively injected into each droplet according to the reagent injection method as shown in FIG. 2 to activate reaction. The incubation of microwell array chip was conducted at the temperature of 35° C., and the test results were obtained by means of fluorescence imaging. The test results were analyzed. Higher inhibition to Caspase-1 enzyme by aforesaid compounds results in weaker activity of enzyme, and thus results in weaker fluorescent signal as shown in FIG. 3. Therefore, compounds numbered 28, 30 and 32 were identified as inhibitors through screening.

Embodiment 2

Figure 4:
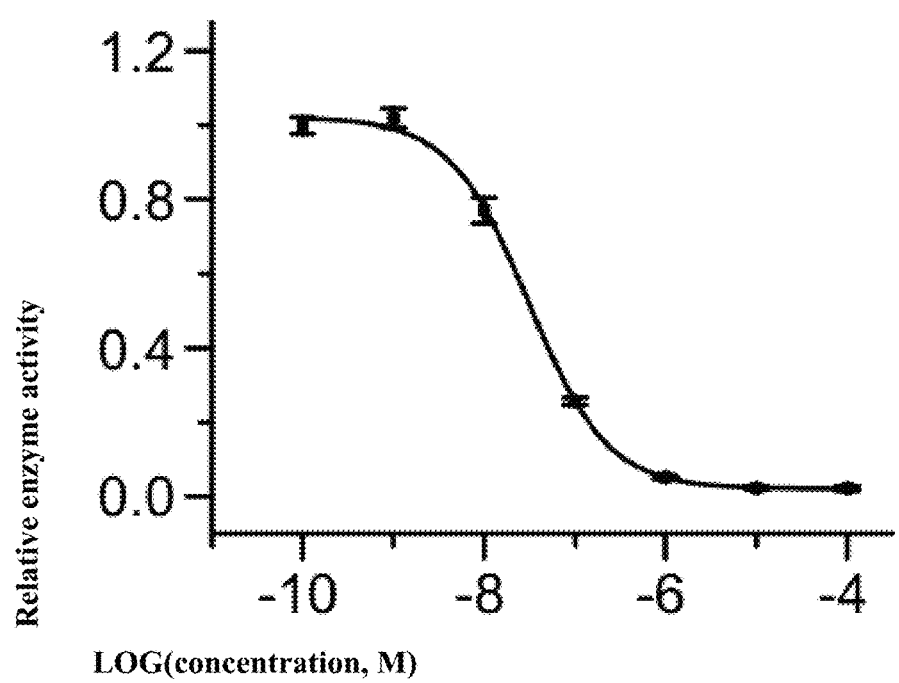
FIG. 4 is the recording chart showing measured half maximal inhibitory concentration ($IC_{50}$) of inhibitor 28 as obtained through screening.

FIG. 4 is the recording chart showing measured half maximal inhibitory concentration ($IC_{50}$) of compound 28 against Caspase-1 enzyme . First, the compound 28 with concentrations of 0.1 nM, 1 nM, 10 nM, 100 nM, 1 µM and 10 µM was added into the sample/reagent storage tubes, respectively. Droplets (180 picoliters) of compound 28 with different concentrations were generated on the microwell array chip with the droplet array screening system and its application method as shown in FIGS. 1 and 2, and 180 picoliters of Caspase-1 enzyme (6 mU/µL) and substrate (Z-YVAD-R110) solution (20 µM) were respectively injected into each droplet to activate reaction. Extraction and normalization of fluorescence value were conducted with reference to the fluorescence image as obtained with the method in Embodiment 1. The logarithmic processing of the concentrations of compound 28 was conducted for plotting the obtained results together with normalized fluorescence values corresponding to the concentrations. Sigmoidal fitting was conducted to the chart with data processing software to obtain the half maximal inhibitory concentration ($IC_{50}$) of 31.6±3.4 nM.

Embodiment 3

Figure 5:
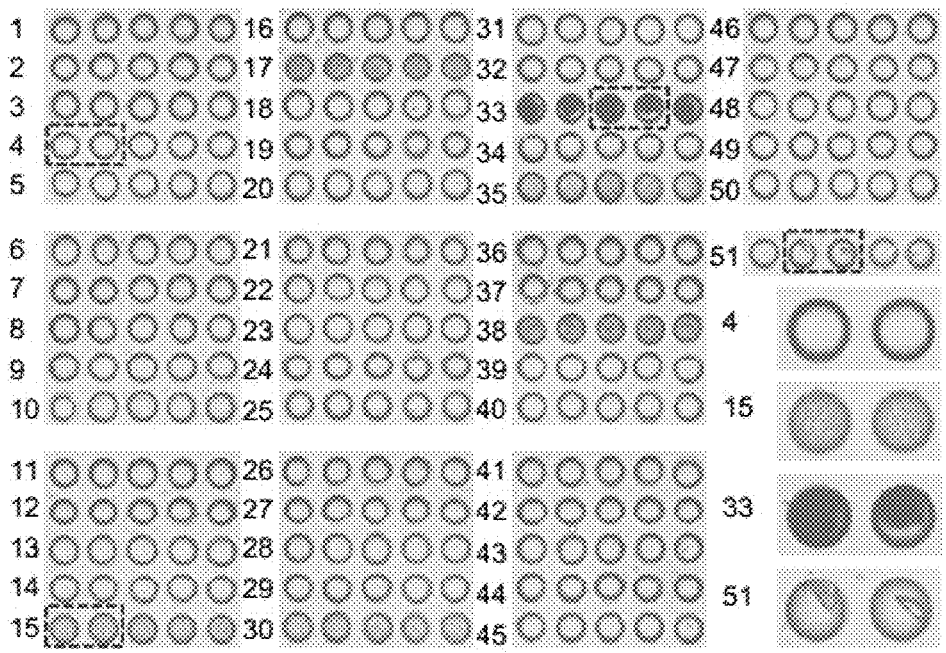
FIG. 5 is the recording chart showing results of screening of protein crystallization conditions by the droplet array screening system in nanoliter scale.

FIG. 5 is the recording chart showing results of screening of protein crystallization conditions by droplet array screening system in nanoliter scale. First, 50 mg/mL lysozyme sample solution and precipitant solutions containing 51 chemical compositions (Crystal crystallization kit from Hampton Company of the U.S.) were added into the sample/reagent storage tubes, respectively. 51 precipitant droplets with volume of 2 nL were generated on the microwell array chip with the droplet array generation method as shown in FIG. 1. Each precipitant condition was repeated for 5 times. After that, 2 nL lysozyme sample solution was respectively injected into each droplet to form crystallization reactors. The chip was placed into a 16° C. incubator for incubation. To prevent evaporation of micro droplets during prolonged incubation, liquid paraffin or mineral oil with poor permeability was selected as the oil phase during test. Finally, the droplet array was examined and imaged with the help of microscope to verify appropriate precipitation conditions for crystallization of lysozyme.

Embodiment 4

Figure 6:
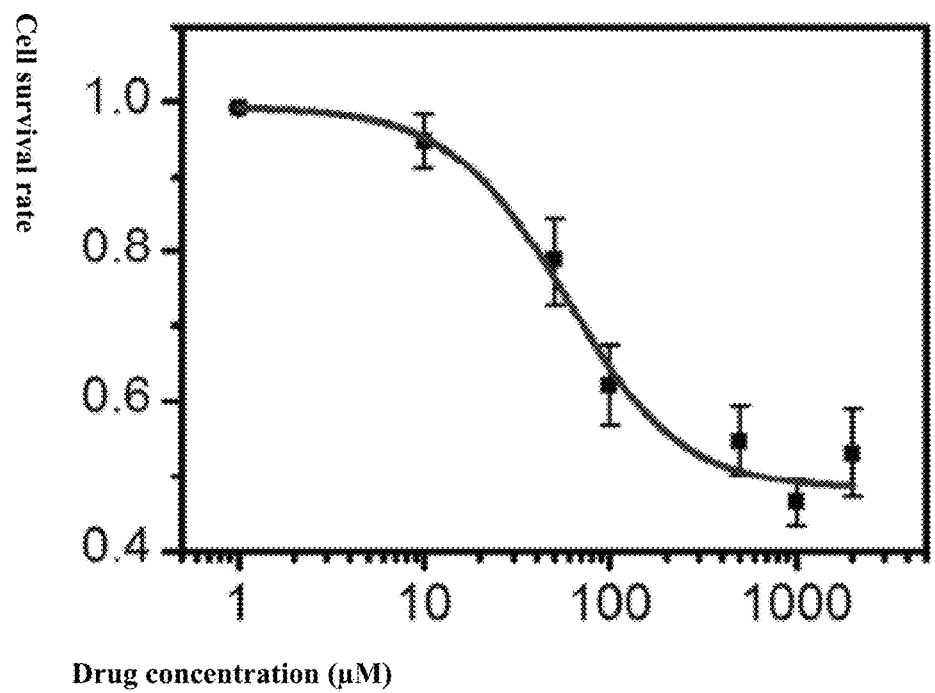
FIG. 6 is the recording chart showing results of cell based pharmaceutical activity studies using the droplet array screening system.

FIG. 6 is the recording chart showing results of cell based pharmaceutical activity studies using the droplet array screening system. FC40 fluorinated oil with higher gas permeability was selected as the oil phase during test to facilitate air exchange as required for cell culture. First, suspension of non-small lung cancer cells A549 was deposited to the array chip with the droplet array generation method as shown in FIG. 1. Each droplet has a volume of 500 nL, containing 80±20 cells. After that, the droplet array chip was placed into the cell incubator for incubation for 24 hours to ensure growth of cells on the chip surface. The droplet array chip with cell fixed to the chip surface was taken out of the incubator; the old cell culture medium in each droplet was removed, and PBS was used to wash off residual medium in the cell droplet; 500 nL 5-fluorouracil pharmaceutical solutions with different concentrations were respectively added into each cell droplet. The droplet array chip was placed into the incubator once again for incubation for another 24 hours. After that, PBS was used to wash off each droplet, and fresh culture medium was added into each droplet for post cell culture. Finally, the capillary was used to respectively remove the cell culture medium in each droplet, and PBS was used for cleaning After that, 500 nL mixed fluorescent dying reagent Calcein AM and Ethidium homodimer-1 were respectively added as required for cell viability test. The droplet array chip was placed into the incubator for incubation for 30 minutes prior to imaging test with the help of microscope. The number of live and dead cells in each droplet was counted to obtain the survival rate of cells following drug stimulation.

The invention claimed is:

1. An application method for an automatic micro droplet array screening system with picoliter scale precision, wherein the system comprises a capillary, a fluid driving system in connection with the capillary, a microwell array chip, a sample/reagent storage tube and an automated translation stage, the application method comprising the following steps:
    (1) filling the fluid driving system and the capillary with a carrier fluid, and removing air bubbles inside the capillary, wherein thermal expansion coefficient of the carrier fluid ranges from 0.00001/° C to 0.0005/° C;
    (2) immersing a sampling end of the capillary into a first oil phase that is mutually immiscible with and above an aqueous sample in the sample/reagent storage tube, and aspirating a plug of the first oil phase into the capillary for separating the aqueous sample and the carrier fluid, wherein the carrier fluid and the first oil phase are mutually immiscible;
    (3) immersing the sampling end of the capillary into the sample/reagent storage tube and aspirating a predetermined volume of the aqueous sample into the capillary; and
    (4) moving the sampling end of the capillary to a location above a second oil phase in and above microwells on the microwell array chip, and pushing the aqueous sample in the capillary into the microwells to form droplets of the aqueous sample, wherein the carrier fluid and the second oil phase are mutually immiscible.

2. The application method for an automatic micro droplet array screening system with picoliter scale precision according to claim 1, wherein step (4) of the application method further comprises the following specific sub-steps:
    producing droplets of multiple aqueous samples to be screened with different chemical compositions or concentrations on the microwell array chip;
    aspirating a predetermined volume of a reagent at one time into the capillary, and respectively inserting the sampling end of the capillary into each aqueous sample droplet; respectively injecting a further predetermined volume of the aspirated reagent to form a droplet reactor, and complete mixing, reaction, testing and screening of the aqueous sample and the reagent.

3. The application method for an automatic micro droplet array screening system with picoliter scale precision according to claim 1, wherein characterized in that step (4) also comprises the following specific sub-steps:
    producing a predetermined number of droplets of a reagent on the microwell array chip;
    respectively injecting the aqueous sample to be screened into each droplet of the reagent to form a droplet reactor, and complete mixing, reaction, testing and screening of the reagent and aqueous sample.

4. The application method for an automatic micro droplet array screening system with picoliter scale precision according to claim 1, wherein the fluid driving system is configured to drive fluid at a flow rate of 1 nanoliter/min to 500 nanoliters/min.

5. The application method for an automatic micro droplet array screening system with picoliter scale precision according to claim 1, wherein an additional volume of the first oil phase is aspirated into the capillary before aspiration of the aqueous sample or a reagent; the first oil phase is also pushed out of the capillary together with the aqueous sample or the reagent.

6. The application method for an automatic micro droplet array screening system with picoliter scale precision according to claim 1, wherein wall thickness of the capillary ranges from 1 micron to 100 microns.

7. The application method for an automatic micro droplet array screening system with picoliter scale precision according to claim 1, wherein the carrier fluid and the first and second oil phases are degassed before step (1).

8. The application method for an automatic micro droplet array screening system with picoliter scale precision according to claim 1, wherein a layer of the second oil phase covers the microwells on the microwell array chip and a layer of the first oil phase covers the aqueous sample in the sample/reagent storage tube; and thickness of the first and second oil phases ranges from 0.1 mm to 10 mm.

9. The application method for an automatic micro droplet array screening system with picoliter scale precision according to claim 1, wherein a biologically compatible surfactant is added into the first and second oil phases; and concentration of the surfactant ranges from 0.01% to 10%.

* * * * *